(12) United States Patent
Adachi et al.

(10) Patent No.: US 8,709,345 B2
(45) Date of Patent: Apr. 29, 2014

(54) SAMPLE ANALYZING DEVICE

(75) Inventors: Sakuichiro Adachi, Kawasaki (JP); Akihisa Makino, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/147,809

(22) PCT Filed: Mar. 1, 2010

(86) PCT No.: PCT/JP2010/001351
§ 371 (c)(1),
(2), (4) Date: Aug. 4, 2011

(87) PCT Pub. No.: WO2010/109772
PCT Pub. Date: Sep. 30, 2010

(65) Prior Publication Data
US 2011/0293476 A1  Dec. 1, 2011

(30) Foreign Application Priority Data
Mar. 25, 2009  (JP) .............................. 2009-073098

(51) Int. Cl.
*G01N 35/02* (2006.01)
*G01N 21/27* (2006.01)
*G01N 21/25* (2006.01)

(52) U.S. Cl.
CPC ............ *G01N 35/025* (2013.01); *G01N 21/272* (2013.01); *G01N 21/274* (2013.01); *G01N 21/253* (2013.01); *G01N 2201/127* (2013.01)
USPC .................. 422/64; 422/63; 436/47; 436/49; 356/432; 356/246

(58) Field of Classification Search
None
See application file for complete search history.

(56) References Cited

U.S. PATENT DOCUMENTS

| 4,451,433 | A |   | 5/1984 | Yamashita et al. |
| 5,037,612 | A | * | 8/1991 | Takahashi et al. .............. 422/64 |
| 5,518,923 | A | * | 5/1996 | Berndt et al. .............. 435/287.3 |
| 2006/0062692 | A1 |  | 3/2006 | Tokieda et al. |

FOREIGN PATENT DOCUMENTS

| CN | 1749757 | 3/2006 |
| JP | 57-082769 | 5/1982 |
| JP | 61-218949 | 9/1986 |
| JP | 05-119039 | 5/1993 |
| JP | 2708437 | 10/1997 |
| JP | 2001-208760 | 8/2001 |
| JP | 2001-235422 | 8/2001 |
| WO | WO 03/093833 | 11/2003 |

* cited by examiner

*Primary Examiner* — P. Kathryn Wright
(74) *Attorney, Agent, or Firm* — Antonelli, Terry, Stout & Krauss, LLP.

(57) ABSTRACT

To reduce measurement time, it may be considered to quicken reaction or speed up analytic determination. In existing analyzing devices, photometry is performed, typically, about every 15 seconds, so that it has not been possible to secure satisfactory reproducibility. Namely, reducing the measurement time and securing reproducibility have not been compatible. It has therefore been desired to increase the number of times of measurements performed in a short period of time. A cell disk is controlled to stop at a position for photometry during the time after a sample and a reagent are mixed and before measurement is finished and, while the cell disk is stopped, photometry is performed once or plural times thereby increasing the total number of times of measurements.

6 Claims, 7 Drawing Sheets

FIG. 7

| USER ID | MEASUREMENT ITEM | PREDICTED VALUE | ANALYZED VALUE | RE-INSPECTION |
|---|---|---|---|---|
| ⋮ | ⋮ | ⋮ | ⋮ | ⋮ |

ALARM!

USER ID xxxx, MEASUREMENT ITEM wwww
PREDICTED VALUE EXCEEDS REFERENCE RANGE.
DO YOU PERFORM RE-INSPECTION?

[Yes] [No]

SAMPLE ANALYZING DEVICE

TECHNICAL FIELD

The present invention relates to a sample analyzing device for analyzing the amount of a component of a sample, for example, an automatic analyzing device for analyzing the amount of a component of blood or urine.

BACKGROUND ART

To analyze the amount of a component of a sample, automatic analyzing devices are widely used. In such automatic analyzing devices: a sample or a reaction solution prepared by mixing a sample and a reagent is irradiated with light emitted from a light source; the amount of light of a single wavelength or each of plural wavelengths transmitted through the sample or reaction solution is measured using a light receiving element; the absorbance of the sample or reaction solution is calculated; and the amount of the component of the sample is determined based on the relationship between absorbance and concentration (see the patent literature 1, for example). In the automatic analyzing devices: many cells each containing a reaction solution are circumferentially arranged on a cell disk which repeats rotating and stopping; and, while the cell disk is rotating, the amount of light transmitted through the reaction solution contained in each cell crossing a measuring position is measured. In this way, each cell crosses the measuring position, typically, once every 15 seconds to be subjected to the photometry. As a result, the amount of light transmitted through the reaction solution contained in each cell is photometrically measured about 40 times in a total time period of 10 minutes per reaction. Based on the variation with time in the amount of light transmitted through the reaction solution and the Lambert-Beer law, the absorbance of the reagent solution is calculated and the amount of the component of the sample is determined.

The patent literature 2 discloses a technique applicable to a highly active sample which completes reaction during a rotation of a disk. In the technique, during the time used by a reaction cell to pass a measuring system, the measuring system is controlled at high speed to measure the absorbance of the reaction cell plural times.

The patent literature 3 discloses a technique in which plural detectors are arranged around a rotating body with reaction cells arranged thereon. In the technique, when the rotating body controlled to rotate and stop is stopped for a predetermined amount of time, reaction cells are measured sequentially by the detectors disposed where they are stopped.

In the field of such automatic analyzing devices, demand has recently been rising for speedy inspection so as to improve operational efficiency in inspection rooms and services for patients and, hence, measurement time reduction and secured reproducibility have been requested.

CITATION LIST

Patent Literature

Patent Literature 1: US Patent No. 4451433
Patent Literature 2: Japanese Patent Application Laid-Open Publication No. 2001-235422
Patent Literature 3: Japanese Patent Application Laid-Open Publication No. 2001-208760

SUMMARY OF INVENTION

Technical Problem

To reduce measurement time, it may be considered to carry out quantitation based on data obtained in an early stage of reaction of a reaction solution. In existing automatic analyzing devices, photometry is performed during a rotation of a cell disk occurring, typically, about every 15 seconds, and quantitation is carried out based on the difference between data obtained in an early stage of reaction of a reaction solution and data obtained when the reaction is over. Generally, the variation with time during an early stage of reaction of a reaction solution is not large, so that quantitation based only on data obtained by photometry performed in an early stage cannot secure satisfactory reproducibility. Namely, reducing the measurement time and securing reproducibility have not been compatible. It has therefore been desired to increase the time used for measurement during an early stage of reaction of a reaction solution.

The patent literature 2 discloses a technique for enabling photometry to be performed plural times during a specific time period while reaction of a reaction solution is taking place. However, increasing the rotation speed of a cell disk and performing photometry plural times is not effective in increasing the photometry time for every cell during a specific time period. It is only effective in increasing the photometry time for some of the cells arranged on the cell disk. Furthermore, increasing the rotating speed of the cell disk results in shortening the time during which each cell passes a measurement position, so that measurement reproducibility decreases.

In the technique disclosed in the patent literature 3, an analyzing device including plural measuring units is used. Including plural measuring units in an analyzing device, however, has not been practical because doing so increases the cost of the analyzing device while making constant measurement correction necessary to correct measurement variations between plural measuring units.

Thus, no technique has been disclosed which, using a same measuring unit, can increase, for every cell, the photometry time within a specific time period during a reaction process of a sample.

Solution to Problem

According to the present invention, a cell disk is controlled to stop at a position for photometry during the time after a sample and a reagent are mixed and before measurement is finished and, while the cell disk is stopped, photometry is performed once or plural times thereby increasing the total number of times photometry is performed. Namely, the sample analyzing device according to the present invention comprises: a plurality of cells each for retaining a reaction solution containing a sample and a reagent mixed together; a cell disk which repeats rotating and stopping with the plurality of cells circumferentially arranged thereon; a drive unit for driving the cell disk; a measuring unit for measuring light obtained by irradiating the reaction solution with light; a cleaning unit for removing the reaction solution from each of the plurality of cells and cleaning the each cell; a data storage unit for storing data; a data processing unit for analyzing, based on data obtained by the measuring unit, an amount of a component of the sample; and an output unit for outputting a result of analysis by the data processing unit. In the sample analyzing device: the driving unit repeats rotating and stopping the cell disk between when the sample and the reagent are mixed and when the reaction solution is removed at the cleaning unit, at least once stopping the cell disk at a photometry position of the measuring unit; and the measuring unit measures the reaction solution both while the cell disk is rotating and while the cell disk is stopped.

The measuring unit performs photometry while the cell disk is stopped and stores an amount of variation with time in data obtained in the data storage unit; and the data processing unit determines an amount of a component of the sample. Furthermore, the measuring unit performs photometry a plurality of times while the cell disk is stopped; and the data processing unit determines an amount of a component of the sample based on an average value of measurements obtained while the cell disk is stopped and a measurement obtained while the cell disk is rotating.

The data storage unit stores both a first calibration curve plotted based on data obtained at the measuring unit while the cell disk is stopped, and a second calibration curve plotted based on data obtained at the measuring unit while the cell disk is rotating; and the data processing unit determines an amount of a component of the sample using the first calibration curve and the second calibration curve. The data storage unit stores sample-versus-stop duration data to be applied in changing, depending on a component to be measured of the sample, an amount of time for photometry to be performed while the cell disk is stopped.

The output unit displays, while the each cell containing the reaction solution is stopped, a result of amount determining analysis by the data processing unit. When an amount of a component of the sample determined by the data processing unit falls outside a predetermined reference range stored in the data storage unit, the output unit can display an alarm on a screen.

Advantageous Effects of Invention

According to the present invention, quantitation in a short period of time is enabled, so that operational efficiency in inspection rooms and services for patients can be improved through speedy inspection.

BRIEF DESCRIPTION OF DRAWINGS

FIG. 7 shows an example display for user.

DESCRIPTION OF EMBODIMENTS

Figure 1:
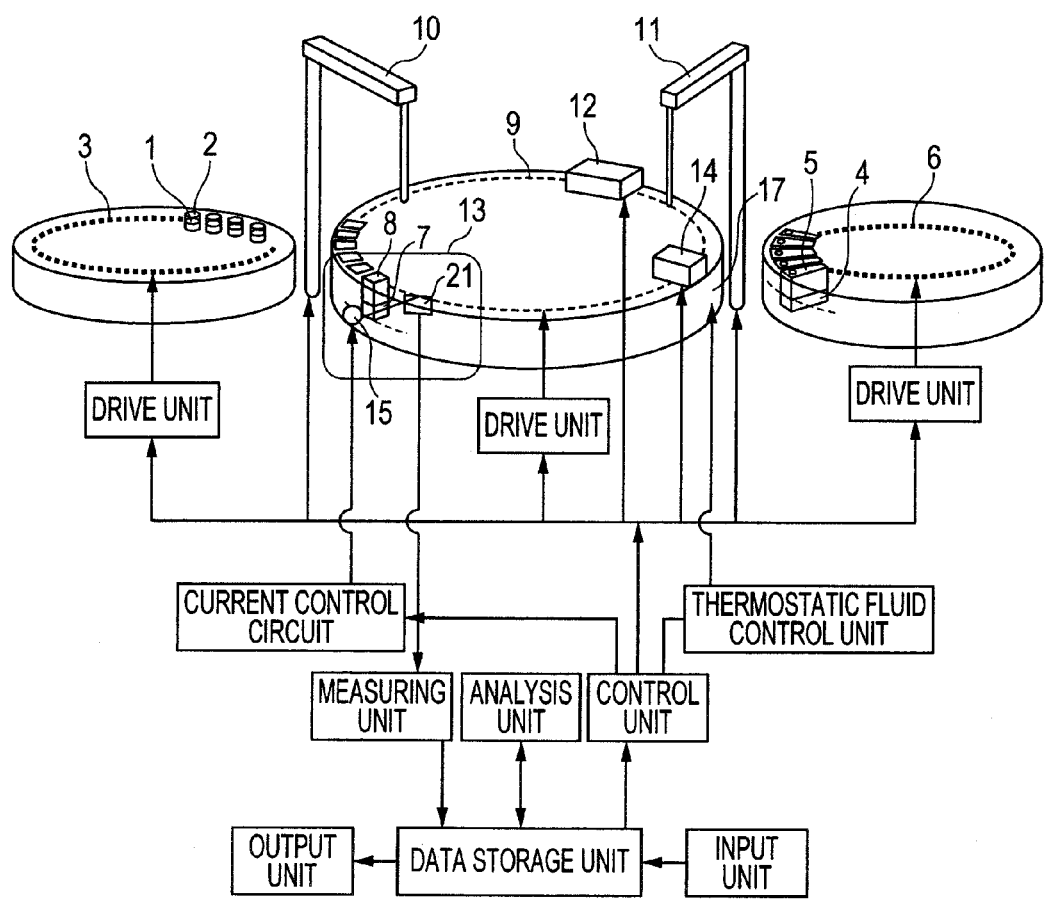
FIG. 1 is a simplified schematic diagram showing an overall configuration of a sample analyzing device according to the present invention.

An embodiment of the present invention will be described below with reference to drawings.
First Embodiment FIG. 1 is a simplified schematic diagram showing an overall configuration of a sample analyzing device according to the present invention. A sample disk 3 carries plural sample cups 2 each containing a sample 1. A reagent disk 6 carries plural reagent bottles 5 each containing a reagent 4. A cell disk 9 carries plural cells 8 in each of which a reaction solution 7 is prepared by mixing the sample 1 and the reagent 4. A sample dispensing mechanism 10 moves a predetermined volume of the sample 1 from a sample cup 2 to a cell 8. A stirring unit 12 stirs, for mixing, the sample 1 and the reagent 4 contained in the cell 8. A measuring unit 13 includes a light emitting unit 15 for emitting light to the reaction solution 7 and a light receiving element 21 for receiving the light transmitted through the reaction solution 7. When the solution contained in the cell has been analyzed, the cell is cleaned at a cleaning unit 14. Subsequently, the cell 8 has a next sample dispensed from the sample dispensing mechanism 10 and a new reagent dispensed from a reagent dispensing mechanism 11. The cell 8 is moved in a state of being dipped in a constant temperature fluid 17 contained in a thermostatic bath in which the fluid temperature and flow rate are controlled by a thermostatic fluid control unit, so that, while being moved, the cell 8 and the reaction solution 7 contained in the cell 8 are kept at a constant temperature. The constant temperature fluid 17 is water kept at a reaction temperature of 37±0.1° C.

The analyzing device also includes a current control circuit which supplies a predetermined amount of current to the light emitting unit, a control unit which controls various units of the analyzing device, a drive unit which rotationally drives each of the sample disk, reagent disk, and cell disk independently in accordance with instructions received from the control unit, the thermostatic fluid control unit for controlling the temperature and flow rate of the constant temperature fluid, the measuring unit for calculating absorbance based on the amount of light received by the light receiving element 21, a data storage unit which stores, for example, data measured by the measuring unit such as reaction process data representing variation with time in the absorbance of the reaction solution and calibration curve data for each measurement item, an input unit which is used to input required data to the data storage unit, an analysis unit which determines a component amount based on the absorbance data, and an output unit which can display and output data.

To determine the amount of a component of the sample 1, the following procedure is used. First, a predetermined amount of the sample 1 in the sample cup 2 is dispensed into the cell 8 by the sample dispensing mechanism 10. Next, a predetermined amount of the reagent 4 in the reagent bottle 5 is dispensed into the cell 8 by the reagent dispensing mechanism 11. When dispensing the sample 1 and reagent 4, the sample disk 3, reagent disk 6, and cell disk 9 are, under the control of the control unit, rotationally driven by the respective drive units so as to move the sample cup 2, reagent bottle 5, and the cell 8 to positions accessible by the respective dispensing mechanisms. Subsequently, the sample 1 and reagent 4 in the cell 8 are stirred by the stirring unit 12 to prepare the reaction solution 7. Even though, in FIG. 1 which is a simplified diagram, only one reagent disk and one reagent dispensing mechanism are shown, the analyzing device typically includes two reagent disks, two reagent dispensing mechanisms, and two stirring units. Depending on the manner in which a sample reacts, the analyzing device may include more than two reagent disks.

In the following, a reagent made to react with a sample first will be referred to as a first reagent, and a reagent made to react with the sample next will be referred to as a second reagent. Normally, the absorbance of the reaction solution 7 is measured every time the cell 8 passes the measuring position of the measuring unit 13 while the cell disk 9 is rotating, and the measurements obtained are sequentially accumulated as reaction process data in the data storage unit. After this photometry process is continued, for example, for about ten minutes, the inside of the cell 8 is cleaned by the cleaning mechanism 14, then the cell 8 can be used for next analysis. Or, if necessary, another reagent 4 may be additionally dispensed into the cell 8 by the reagent dispensing mechanism 11 after a predetermined amount of time to subsequently have the mixture in the cell 8 stirred by the stirring unit 12 and subject the stirred mixture to further measurement for a predetermined amount of time. This makes it possible to store reaction process data representing the absorbance values of the reaction solution 7 measured at a predetermined interval in the data storage unit. The reaction process data thus accumulated is used for component analysis performed at the analysis unit based on calibration curve data by inspection item. Data required to control various units and to perform various analyses is inputted from the input unit to the data storage unit. The calibration curve data is stored in the data storage unit. Various data, analysis results, and alarms are outputted, for example, displayed, by the output unit.

Figure 2:
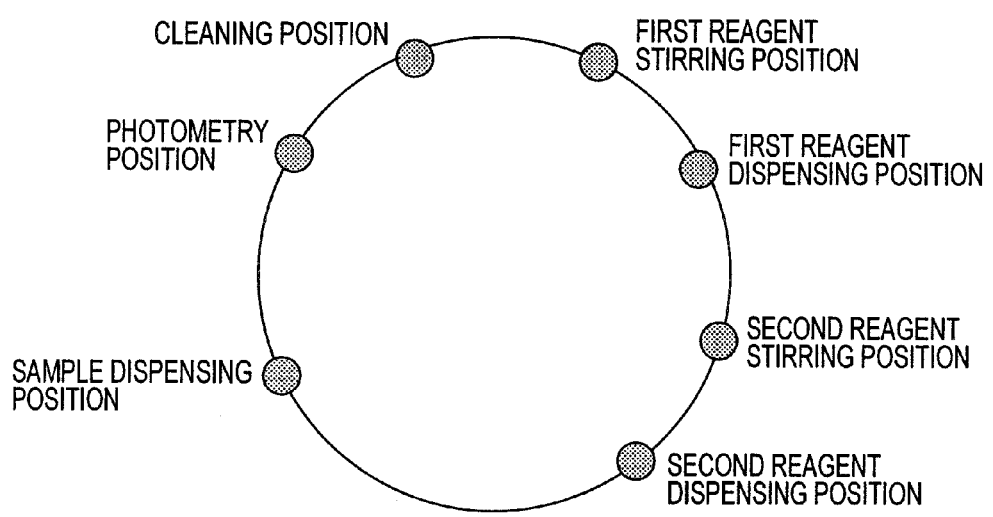
FIG. 2 is a diagram showing analysis operations performed on various parts of a cell disk included in the sample analyzing device according to the present invention.

FIG. 2 shows example positions for analysis operations performed on various parts of the cell disk, while the cell disk is stopped, of the sample analyzing device according to the present invention. The main stopping positions of the cell disk include positions for dispensing a sample, a first reagent and a second reagent, positions for stirring the reaction solution after the first reagent is dispensed and after the second reagent is dispensed, respectively, and a photometry position for photometry by a photometry unit. According to the present invention, control is performed such that, after a sample and a reagent are mixed, the cell holding the reaction solution is positioned at a photometry position so as to enable photometry while the cell disk is stopped.

Figure 3:
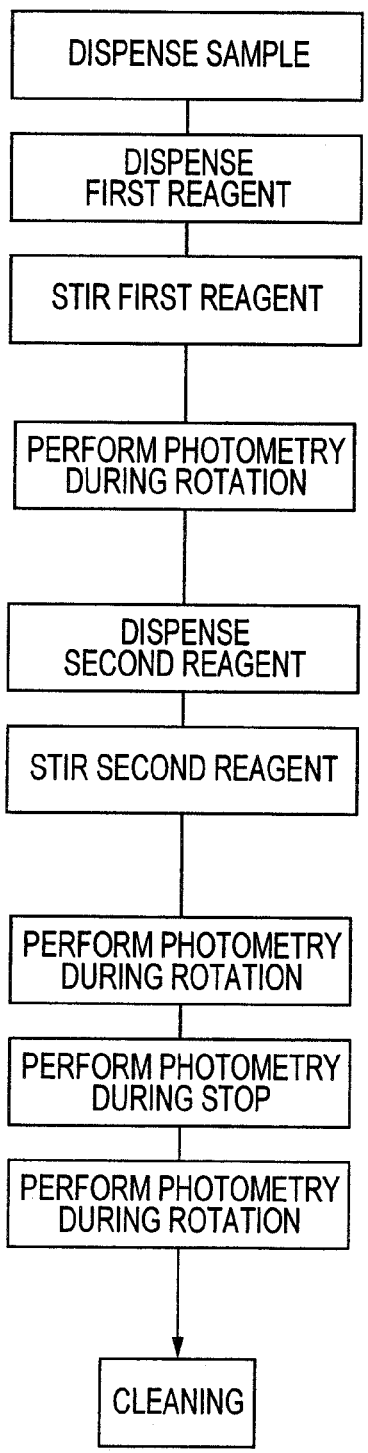
FIG. 3 is a diagram showing an analysis operation sequence according to the present invention.

FIG. 3 shows an analysis operation sequence according to the present invention.

After a sample is dispensed into a cell, a first reagent is added to the cell and the mixture in the cell is stirred. Subsequently, after data obtained by photometry performed while the cell disk is rotating is stored as photometry data obtained during rotation, a second reagent is added to the cell and the resultant mixture in the cell is stirred. Photometry is performed again while the cell disk is rotating to obtain photometry data during rotation. During this process, control is performed to stop the cell at a photometry position so as to obtain photometry data while the cell disk is stopped and add the data to the photometry data obtained while the cell disk is rotating as the reaction process data. Finally, at a cleaning position, the reaction solution contained in the cell is removed and the cell is cleaned.

Figure 4:
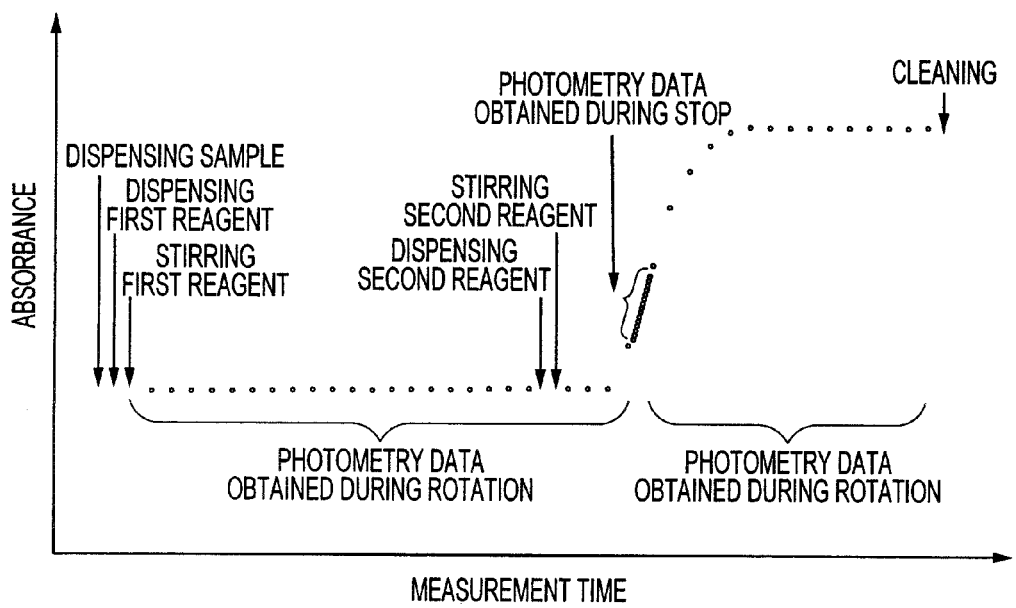
FIG. 4 shows reaction process data according to the present invention.

FIG. 4 shows an analysis operation sequence along with the reaction process data obtained using the sequence shown in FIG. 3. The data shown in FIG. 4 includes the photometry data obtained, after the sample and the first reagent are dispensed into the cell and the mixture in the cell is stirred, while the cell disk is rotating and the photometry data obtained, after the second reagent is added into the cell and the resultant mixture in the cell is stirred, while the cell disk is rotating. The above photometry data obtained while the cell disk is rotating is added to the photometry data obtained while the cell disk is stopped. This differentiates the sample analyzing device of the present invention from existing sample analyzing devices. In the example shown in FIG. 4, after the second reagent is dispensed and the resultant mixture is stirred, photometry is performed while the cell disk is rotating and also while the cell disk is stopped. The timing of photometry to be performed after stopping the cell disk at the position of the photometry unit depends on the target sample and the reagent to be used. Information on such timing may be stored beforehand in the data storage unit or may be set from the input unit by the user. When photometry is performed while the cell disk is rotating, measurement can be made only during the time when the cell passes the photometry position. When photometry is performed while the cell disk is stopped, prolonged photometry, for example, one-second photometry can be performed to obtain data. This makes it possible to measure variation in the amount of light or determine an average amount of light transmitted through the reaction solution while the cell disk is stopped.

In the technique disclosed in the patent literature 2, during disk rotation, a measuring system is driven at high speed for a predetermined amount of time. The technique, however, involves a problem that the time length per photometry is short to result in reduced reproducibility. According to the present invention, the photometry time is increased, so that reproducibility is not reduced.

Figure 5:
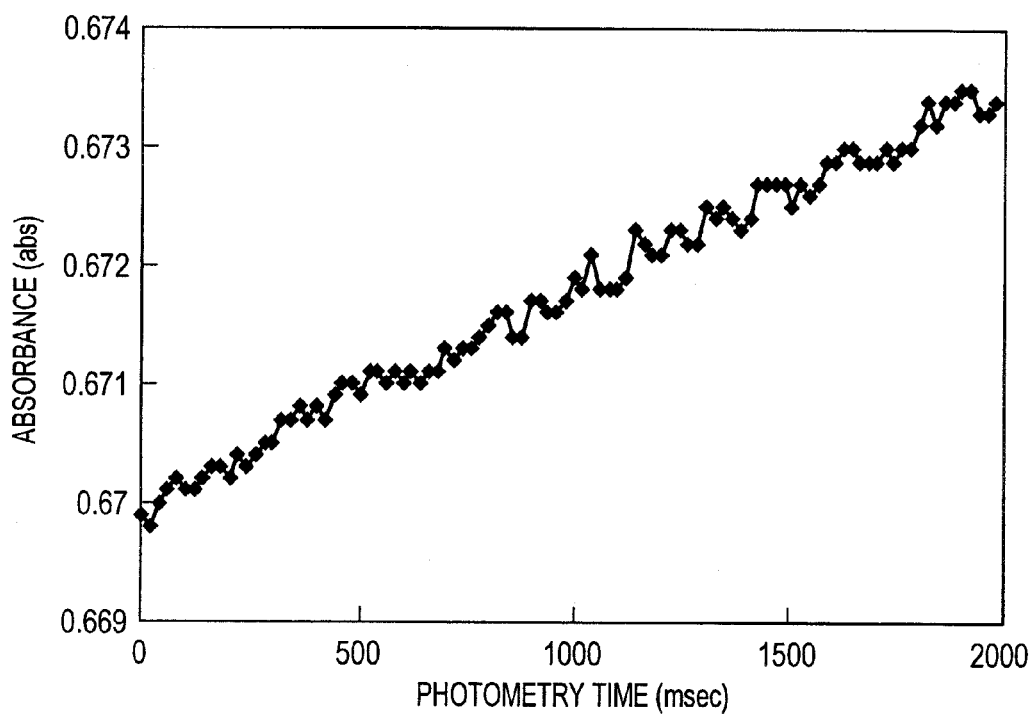
FIG. 5 shows photometry data obtained during a stop.

FIG. 5 shows example photometry data obtained while the disk is stopped. A CRP reagent (Nanopia CRP made by Sekisui Chemical Co., Ltd.) was used as a latex item and a CRP calibrator (made by Sekisui Chemical Co., Ltd.) with a concentration of 3 mg/dL was used as a sample. The data represents the results of performing photometry at a wavelength of 570 nm 100 times during the two seconds between about 45 seconds after dispensing of a second reagent and about 47 seconds after dispensing of the second reagent.

As described above, by performing photometry while the disk is stopped after a sample and reagents are mixed, data on absorbance variation during a reaction can be obtained. Thus, it is possible to obtain calibration curve data based only on photometry data obtained while the disk is stopped and perform quantitative measurement on the sample.

The absorbance slope obtained by performing photometry 100 times in two seconds was plotted with respect to concentration and the plotted data is stored in the data storage unit as a calibration curve.

Figure 6:
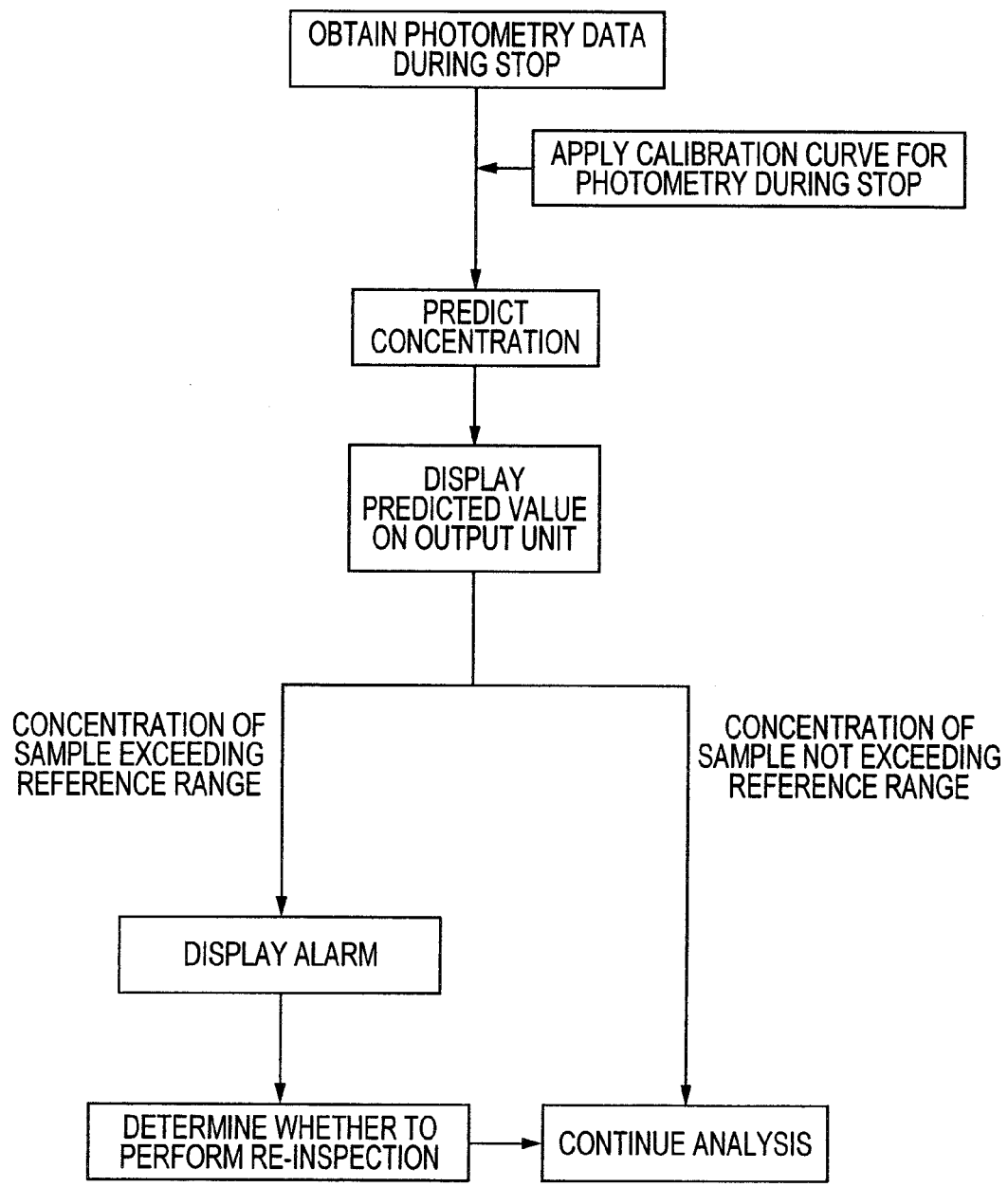
FIG. 6 is a flowchart of a process performed using photometry data obtained during a stop.

Alternatively, a calibration curve may be plotted, for storing in the data storage unit, using an average value of the data obtained by performing photometry 100 times while the disk is stopped together with photometry data obtained by performing photometry while the disk is rotating. In this case, an average value of 100 measurements is used as the photometry data obtained while the disk is stopped, so that the measurement error can be reduced to 1/10 relative to the error occurring in a single measurement. Based on the calibration curve thus obtained, the amount of a component of the sample can be determined using data obtained while the disk is stopped and the determined results can be displayed on a screen. The concentration data determined based on the absorbance slope plotted using photometry data obtained while the disk is stopped can be outputted before the sample completes reacting with the reagent, so that the measurement time can be reduced. A flowchart of this process is shown in FIG. 6. There is a need for early availability of concentration data so that, when a concentration exceeding a reference range is obtained, necessary re-inspection or treatment can be carried out. It is therefore helpful that a predicted concentration value can be outputted before the sample completes reaction.

Also, when the amount of a component of a sample calculated from the photometry data obtained while the disk is stopped falls outside a predetermined reference range, an alarm can be displayed on a screen, for example, to urge re-inspection. This allows the operator of the sample analyzing device to obtain information obtained by the photometry being performed earlier than in cases where existing analyzing devices are used, so that operational efficiency in inspection rooms can be improved. Data on a reference range may be stored in the data storage unit beforehand or may be inputted by the user from the input unit. FIG. 7 shows an example of alarm display.

Since calibration curves plotted both from photometry data obtained while the disk is stopped and from photometry data obtained, as in ordinary cases, while the disk is rotating are retained, both an early result of analysis and a final result determined by an existing method after completion of reaction of the sample can be obtained. Hence, an overall result of analysis can be determined with higher accuracy.

In general cases of CRP measurement, the amount of CRP is determined based on the difference between photometry data obtained 45 seconds and 300 seconds after a second reagent is dispensed. According to the present invention, the amount of CRP is determined based on the difference between the average value of photometry data obtained by performing photometry 100 times while the disk is stopped during the time from 45 seconds after dispensing of a second agent to 47 seconds after dispensing of the second agent and the value of photometry data obtained 300 seconds after dispensing of the second agent. In this way, noise in the measuring unit can be reduced to 1/10 compared with when using photometry data obtained by one measurement, so that reproducibility is improved. Furthermore, the time during which the disk is stopped may be extended for a specific measurement item. In cases where the amount of a component to be measured is expected to be very small and therefore it is desired to secure an adequate time for photometry to be performed while the disk is stopped, extending the time during which the cell disk is kept stopped makes it possible to obtain data with high reproducibility. Data required in changing, depending on the component to be measured of a sample or the amount of the component, the time length for photometry to be performed while the disk is stopped may be stored beforehand in the data storage unit or may be inputted from the input unit by the user.

Even though analysis can be made anytime after a reagent and a sample are mixed until the cell containing the sample is cleaned, until about 30 seconds pass after the reagent and the sample are mixed, the reaction of the sample with the reagent is not stable due to an initial uneven state of the mixture. Also, when one minute or so passes after the reagent and the sample are mixed, the absorbance variation resulting from the sample's reaction with the reagent becomes smaller. Hence, performing photometry while the disk is stopped during the time between 30 seconds after and one minute after the last one of plural reagents to be added is mixed makes it possible to obtain highly reproducible data more speedily. Data on the timing of photometry may be stored in the data storage unit beforehand or may be inputted from the input unit by the user. As described above, performing photometry while the disk is stopped using a same measuring unit as the one used to perform photometry while the disk is rotating makes it possible to measure absorbance variations for all cells during a same specific time period. This allows a predicted measurement value to be speedily calculated and contributes toward improving inspection room convenience.

REFERENCE SIGNS LIST

1 . . . Sample
2 . . . Sample cup
3 . . . Sample disk
4 . . . Reagent
5 . . . Reagent bottle
6 . . . Reagent disk
7 . . . Reaction solution
7a to 7c . . . Reaction solution
8 . . . Cell
8a to 8c . . . Cell
9 . . . Cell disk
10 . . . Sample dispensing mechanism
11 . . . Reagent dispensing mechanism
12 . . . Stirring unit
13 . . . Measuring unit
14 . . . Cleaning unit
15 . . . Light emitting unit
16 . . . Light
17 . . . Constant temperature fluid
21 . . . Light receiving element

The invention claimed is:

1. A sample analyzing device, comprising:
a plurality of cells each for retaining a reaction solution containing a sample and a reagent mixed together;
a cell disk which repeats rotating and stopping with the plurality of cells circumferentially arranged thereon;
a drive which drivingly rotates and stops the cell disk;
a single measuring unit which irradiates light to the reaction solution in respective cells and obtains a measurement thereof at a single photometry position;
a cleaning unit which removes the reaction solution from each of the plurality of cells and which enables cleaning the each cell;
a data storage which stores data;
a data processing unit which analyzes, based on data obtained by the measuring unit, an amount of a component of the sample;
an output unit which outputs a result of analysis by the data processing unit; and
a controller which controls the drive so as to enable the drive to repeat rotating and stopping of the cell disk between when the sample and the reagent are mixed and when the reaction solution is removed at the cleaning unit, at least once stopping of the cell disk at the photometry position of the measuring unit so that the measuring unit measures the reaction solution of at least one cell both while the cell disk is rotating and while the cell disk is stopped;
wherein the data storage unit stores both a first calibration curve plotted based on data obtained at the measuring unit while the cell disk is stopped, and a second calibration curve plotted based on data obtained at the measuring unit while the cell disk is rotating; and
wherein the data processing unit determines an amount of a component of the sample using the first calibration curve and the second calibration curve stored in the data storage unit.

2. The sample analyzing device according to claim 1, wherein: the measuring unit performs photometry while the cell disk is stopped and stores an amount of variation with time in data obtained in the data storage unit; and the data processing unit determines an amount of a component of the sample.

3. The sample analyzing device according to claim 1, wherein: the measuring unit performs photometry a plurality of times while the cell disk is stopped; and the data processing unit determines an amount of a component of the sample based on an average value of measurements obtained while the cell disk is stopped and a measurement obtained while the cell disk is rotating.

4. The sample analyzing device according to claim 1, wherein the data storage stores sample-versus-stop duration data to be applied in changing, depending on a component to be measured of the sample, an amount of time for photometry to be performed while the cell disk is stopped.

5. The sample analyzing device according to claim 1, wherein the output unit displays, while the each cell containing the reaction solution is stopped, a result of amount determining analysis by the data processing unit.

6. The sample analyzing device according to claim 1, wherein, when an amount of a component of the sample determined by the data processing unit falls outside a predetermined reference range stored in the data storage unit, the output unit can display an alarm on a screen.

* * * * *